US00PP13387P2

(12) United States Plant Patent

Anderson et al.

(10) Patent No.: US PP13,387 P2
(45) Date of Patent: Dec. 17, 2002

(54) CHRYSANTHEMUM PLANT NAMED '92-296-25'

(75) Inventors: Neil Owen Anderson, St. Paul, MN (US); Peter David Ascher, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/503,364

(22) Filed: Feb. 14, 2000

(51) Int. Cl.[7] ..... A01H 5/00
(52) U.S. Cl. ..... Plt./286
(58) Field of Search ..... Plt./286

(56) References Cited

U.S. PATENT DOCUMENTS

| | | | |
|---|---|---|---|
| PP7,513 | P | 4/1991 | VandenBerg |
| PP7,754 | P | 12/1991 | VandenBerg |
| PP8,759 | P | 5/1994 | VandenBerg |
| PP9,445 | P | 1/1996 | VandenBerg |
| PP10,848 | P | 4/1999 | VandenBerg |
| PP10,909 | P | 5/1999 | Wain |
| PP10,943 | P | 6/1999 | Fuess |
| PP11,009 | P | 7/1999 | Davino, Jr. |
| PP11,032 | P | 8/1999 | Glicenstein |

OTHER PUBLICATIONS

Peter Ascher, et al., Maxi–Mums A Horticultural Breakthrough!, Minnesota Report 242–1997 University of Minnesota, Distribution Center Publication MR–67280B Minnesota Agricultural Experiment Station University of Minnesota (1997).
R.B. Clark, History of Culture of Hardy Chrysanthemums, National Chrysanthemum Society 18(3):144, 1962.
W.W. Garner, et al., Flowering and Fruiting of Plants as Controlled By The Length Of Day, 1920, p. 377–400, Yearbook of the Department of Agriculture, 1920, USA.
Peter Ascher, et al., Breeding and New Cultivars, Academic Perspective, Tips on Growing and Marketing Garden Mums, Ohio Florist's Association 1996.
Bradford Bearce, et al., Chrysanthemums A Manual of the Culture, Diseases, Insects and Ecocomics of Chrysanthemums, Jun. 1964, pp. 6–19, Prepared for The New York State Extension Service Chrysanthemum School with the Cooperation of the New York State Flower Growers Association, Inc.
Neil O. Anderson, et al., Rapid Generation Cycling of Chrysanthemum Using Laboratory Seed Development and Embryo Rescue Techniques, Journal of the American Society of Horticultural Science, Mar. 1990, pp. 329–336, vol. 115(2), Alexandria, Virginia 22314.
Leon Glicenstein, Breeding and New Cultivars, Commercial Perspective, Tips on Growing and Marketing Garden Mums, Ohio Florist's Association 1996.
M.A. Nazeer, et al., Cytyogenetical Evolution of Garden Chrysanthemum, Current Science, Jun. 20, 1982, Vo. 51, No. 12.
Edward Higgins, Containers and Marketing, Tips on Growing and Marketing Garden Mums, Ohio Florist's Association 1996.
Naomasa Shimotomai, Bastardierungsversuche bei Chrysanthemum I., Journal of Science of the Hiroshima University, Series, B, Div. 2, vol. 1, Art. 3, 1931.
Naomasa Shimotomai, Bastardierungsversuche bei Chrysanthemum II. Eentstehung eines fruchtbaren Bastardes (haploid $4n^2$) aus der Kreuzung von *Ch. marginatum* (hapl. 5n) mit *Ch. morifolium* (hapl. 3n), Journal of Science of the Hiroshima University, Series B, Div. 2, vol. 1, Art. 8, 1932.
Ernest L. Scott, The Breeder's Handbook, 1957, pp. 1–76Handbook No. 4, National Chrysanthemum Society, Inc., U.S.A.
John Woolman, Chrysanthemums For Garden And Exhibition, 1953, pp. 1–103, W.H. & L. Collingridge Ltd., Tavistock Street, London WC2 and Transatlantic Arts Incorporated, Forest Hills, New York.
H.G. Witham Fogg, Chrysanthemum Growing, 1962, pp. 1–171, John Gifford Limited, London, W.C.2.
National Agricultural Statistics Service, USDA Additional Floriculture Information, pp. 1–84, National Agricultural Statistics Service, Floriculture Crops, 1998 Summary, Jun. 1999.
Handbook on Chrysanthemum Classification, A publication of the Classification Committee National Chrysanthemum Society, Inc. U.S.A., 1996 Edition.
C. Ackerson, Chapter 12 Development of the Chrysanthemum in China, pp. 146–155, National Chrysanthemum Society Bulletin 1967.
C. Ackerson, Chapter 11 Original Species of the Chrysanthemum, pp. 105–107, National Chrysanthemum Society Bulletin 1967.
G.J. Dowrick, The Chromosomes of Chrysanthemum, I: The Species, pp. 365–375, Heredity 6:365–375, 1952.

*Primary Examiner*—Bruce R. Campell
*Assistant Examiner*—A Para
(74) *Attorney, Agent, or Firm*—Fish & Richardson, P.C., P.A.

(57) ABSTRACT

A new and distinct Chrysanthemum plant named 92-296-25 is provided. This new cultivar was the result of a unique cross between *Dendranthema×grandiflora* and F1 progeny of a cross between *Dendranthema weyrichii* and *Dendranthema×grandiflora*.

2 Drawing Sheets

BACKGROUND OF THE INVENTION

The present invention comprises a new and distinctive chrysanthemum plant, hereinafter referred to by the cultivar name 92-296-25. This new cultivar was the result of a cross in 1989 between *Dendranthema weyrichii* and *Dendranthema×grandiflora*. More specifically, the breeding program which resulted in the production of the new cultivar was carried out in St. Paul., Minn. The female or seed parent of 92-296-25 was *Dendranthema weyrichii* 'Pink Bomb' (unpatented), commercially available from White Flower Farms, Conn. having the following characteristics: (a) the plant habit is prostrate and the plant spreads via rhizomes to form a large mat after the first year; (b) the plant has a diameter of about 1.5' and is about 5–6" tall; (c) the plant is hardy in zones 4–9 (Southeast)Zone 10 (west); (d) the flower of the plant is a single daisy, having light lavender-colored ray florets and central disc florets with yellow pollen; (e) the plant has leaves that are dark green in color, with a very shiny leaf surface (glossy), and glabrous leaf margins that are deeply incised, and (f) the plant tends to rosette, needs cold treatment to flower consistently, flowering can be sporadic with gaps in the plant architecture and the plant is an obligate short-day plant. The male or pollen parent of 92-296-25 was *Dendranthema×grandiflora*, either 'Crusader' (U.S. Plant Pat. No. 6,531) or 'Adorn' (U.S. Plant Pat. No. 6,059) which is commercially available from Yoder Brothers, Inc., Barberton, Ohio or Pan American Plant Co. Both plants were adjacent to the female parent. 'Crusader' and 'Adorn' each have the following characteristics: (a) the plant habit is cushion; (b) the plant dimensions are similar to other cushion types commercially available from Yoder Brothers, Inc., such as, but not limited to, the variety 'Monterey'; (c) the plants are hardy in zones 6–9 (Southeast)/Zone 10 (west); (d) the flower is a single or duplex daisy, lavender ('Crusader') or deep purple ('Adorn') in color, central disc florets with yellow pollen; (e) the plant has leaves that are similar to other Yoder Brothers, Inc. cushion series chrysanthemums; and (f) the plant is a faculative short-day plant. The resulting seed, identified as 90-287-145 was collected. In 1991, a plant of 90-287-145 was crossed as the male parent with plants identified as 83-267-3, a University of Minnesota *Dendranthema×grandiflora* parental selection (U.S. Plant Pat. No. 6,884), as the female parent and the resulting seeds, identified as cross-number 92-296 (unpatented) were collected. In 1992, seedlings of the cross 92-296 were germinated and flowering progeny were evaluated. 92-296-25 was the twenty-fifth plant from the cross and was selected during the fall of 1992. The parentage of the new cultivar can be summarized as follows:

[*Dendranthema×grandiflora*]×(*Dendranthema weyrichii×Dendranthema×grandiflora*).

Asexual reproduction of the new cultivar by terminal or stem cuttings taken during 1993 through 1999 at St. Paul, Minn., U.S.A. has demonstrated that the characteristics of the new cultivar as herein described are firmly fixed and are retained through successive generations of such asexual propagation.

SUMMARY OF INVENTION

It was found that the cultivar of the present invention:

(a) Exhibits extreme hybrid vigor, (b) Develops, in its second and subsequent years after planting, when grown in the fall under natural day-length and without the application of growth regulators, into a flowering herbaceous shrub having a plant height of from about 2.5 to about 3.0 feet and a spread from about 3.0 to about 7.0 feet, (c) Exhibits, in its second and subsequent years after planting and during the fall season (August–October), a massive floral display, (d) Displays flowers which are singly toned with grey, giving the flower petals a slightly altered coloration, (e) Exhibits superior winter hardiness, including frost tolerance, and (f) Exhibits self-pinching.

The 92-296-25 cultivar has not been observed under all possible environmental conditions to date. Accordingly, it is possible that the phenotype may vary somewhat with variations in the environment, such as temperature, light intensity, and day length.

When the new cultivar of the present invention is compared to 'Emily' (U.S. Plant Pat. No. 7,754), it is found to exhibit a more spreading and prolific habit accompanied with a massive floral display in its second and subsequent years after planting. Reference is made to attached Table 1 which compares certain characteristics of 92-296-25 to 'Emily'.

TABLE 1

| CHARACTERISTIC | 92-296-25 | Emily |
|---|---|---|
| Capitulum form and type | Single daisy | Flat decorative with many ray florets |
| Plant Height | About 19 to 20 inches (first year); about 2.5 to 3.0 feet (second year) | 14 inches |
| Branching Pattern | Spreading and very prolific | Spreading and prolific |
| Flowering Response | 5.5 weeks | 6 weeks |
| Flower diameter | 6 cm | 5.7 to 7.0 cm |
| Ray florets, color, mature | Lavender | Light pink with darker center |

The new cultivar of the present invention is distinguished from its parents by its shrub-like growth in the second and successive years of growth, its superior winter hardiness, frost tolerance, and tendency to attract butterflies. Its parents (830267-3 and 90-287-145) were cushion in habit.

TABLE 2

| Characteristic | 92-296-25 | 83-267-3 | 90-287-145 |
|---|---|---|---|
| Flower Color | Lavender | White | Lavender |
| Flower Type | Daisy | Semi-Double | Daisy |
| Flowering Response | Short Day | Day neutral | Short day |
| Stamens | 141 | 15 | 109 |
| Pistils | 34 | 120 | 31 |
| Seeds/Fruit | | | |
| Number of | 175 | 135 | 140 |
| Shape | Oblanceolate achene | Oblanceolate achene | Oblanceolate achene |
| Color | RHS brown, group 200 D | RHS gray, group 201C | RHS brown, group 200 B |

BRIEF DESCRIPTION OF THE PHOTOGRAPHS

The accompanying photographs show as nearly true as it is reasonably possible to make the same in color illustrations of this type, typical flower and foliage characteristics of the new cultivar. The plants were grown in a greenhouse at St. Paul., Minn., USA.

FIG. 1 shows an adaxial and abaxial views of the leaf shape of chrysanthemum variety 92-296-25.

FIG. 3 is a color photograph of chrysanthemum variety 92-296-25 after two years of growth.

DETAILED BOTANICAL DESCRIPTION

Figure 2:
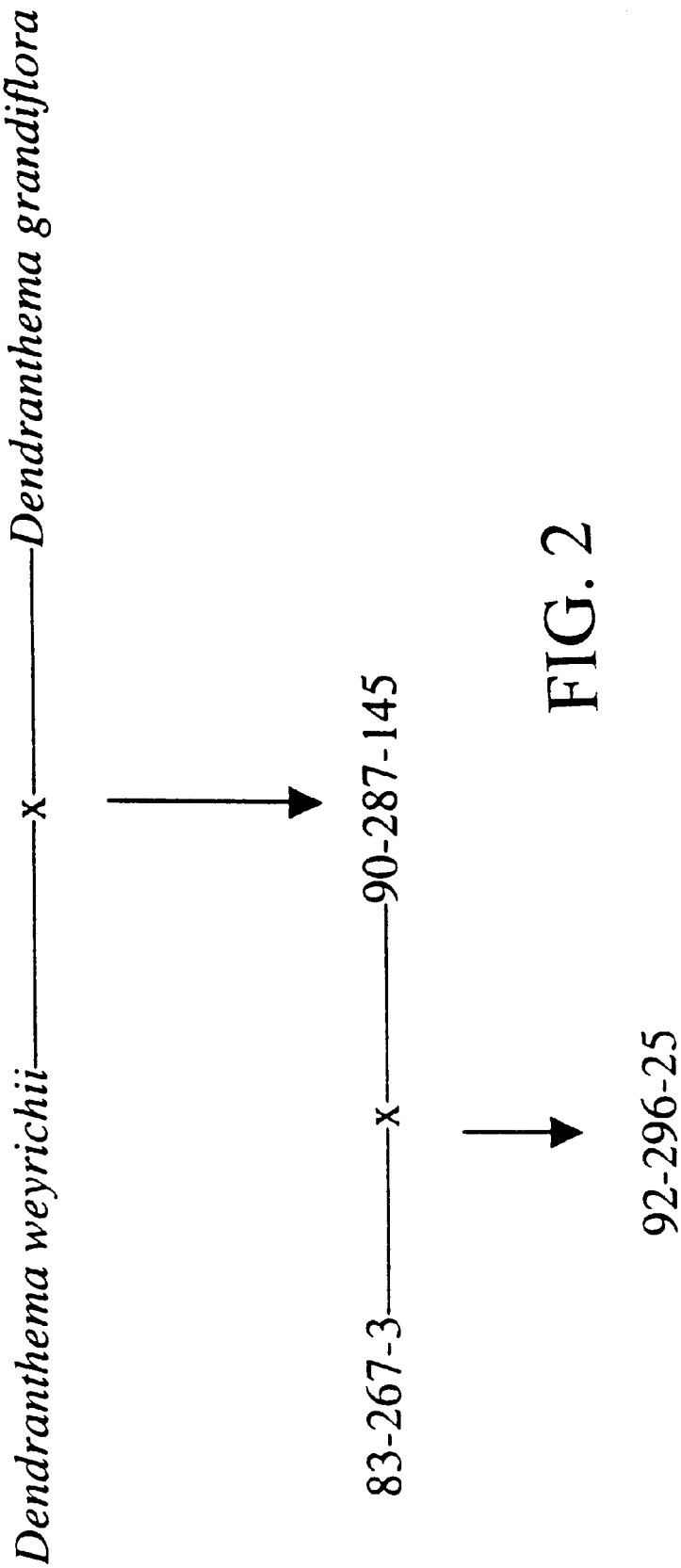
FIG. 2 shows the breeding history of chrysanthemum variety 92-296-25.

The chart used in the identification of colors described herein is The Horticultural Colour Chart issued by the British Colour Council in collaboration with The Royal Horticultural Society, London, England (1938–1941). The color values were determined on Oct. 15, 1999 in St. Paul, Minn. The readings were taken between 1:00 and 3:00 p.m. under approximately 2500 footcandles of light. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:
- *Type.*—Herbaceous stem cutting.
- *Time to rooting.*—About 1 week.
- *Rooting habit.*—Vigorous.

Botanical classification: *Dendranthema×hybrida.*
Commercial classification: Chrysanthemum hybrid.
Plant description:
- *Appearance, shape.*—Loose sphere.
- *Appearance, growth habit.*—Cushion.
- *Appearance, growth rate/vigor.*—Vigorous.
- *Plant height.*—About 19 to about 20 inches (first year) 2.5 to 3.0 feet (second year).
- *Lateral branch length.*—1 to 3.5 feet.
- *Quantity of lateral branches after removal of apical meristem.*—One per node.
- *Stem color.*—RHS Leek Green ooo858/1.

Foliage description:
- *Number of leaves per plant.*—Greater than about 10,000.
- *Number of leaves per lateral branch.*—8 to 30.
- *Leaf arrangement.*—Alternate.
- *Leaf size, fully expanded, length.*—13 cm.
- *Leaf size, fully expanded, width.*—6 cm.
- *Leaf apex.*—Obtuse.
- *Leaf base.*—Cuneate.
- *Leaf margin.*—Incised (Mulberry-like incisions).
- *Leaf texture.*—Hirsute.
- *Petiole length.*—6.8 cm.
- *Color, young foliage adaxial surface.*—RHS Spinach Green o960.
- *Color, young foliage abaxial surface.*—RHS Spinach Green o960/2.
- *Color, fully expanded foliage adaxial surface.*—RHS Ivy Green ooo1060/3.
- *Color, fully expanded foliage abaxial surface.*—RHS Sage Green ooo861/1.
- *Color, venation adaxial surface.*—RHS Sage Green ooo861/1.
- *Color, venation abaxial surface.*—RHS Lavender Green ooo761/1.
- *Color, petiole.*—RHS Lavender Green ooo761.

Inflorescence description:
- *Appearance.*—Head (Composite); single daisy.
- *Flowering response.*—5.5 weeks (short day, SD).
- *Quantity of inflorescences.*—700 to 800 (first year). About 4,000 (second year).
- *Inflorescence size, diameter.*—6 cm.
- *Inflorescence size, depth (height).*—1.6 cm.
- *Inflorescence size, diameter of disc.*—1.1 cm.
- *Opening inflorescences, bud shape.*—Flattened hemisphere to upright tubular.
- *Opening inflorescences, bud size, length.*—0.9 cm.
- *Opening inflorescences, bud size, width.*—0.9 cm.
- *Opening inflorescences, bud color.*—RHS Rhodamine Purple 29/2.
- *Ray florets, shape.*—Linear lanceolate; vertical pleats.
- *Ray florets, size, length.*—2.6 cm.
- *Ray florets, size, width.*—0.5 cm.
- *Ray florets, apex.*—Acuminate.
- *Ray florets, base.*—Attenuate.
- *Ray florets, margin.*—Entire.
- *Ray florets, texture.*—Glabrous.
- *Ray florets, aspect.*—Primarily horizontal; may be slightly upright or pendant.
- *Number of ray florets per inflorescence.*—About 34.
- *Ray florets, color, when opening, adaxial surface.*—RHS Rhodamine Purple 29/3.
- *Ray florets, color, when opening, abaxial surface.*—RHS Cyclamen Purple 30/2.
- *Ray florets, color, mature, adaxial surface.*—RHS Rose Madder 23/3.
- *Ray florets, color, mature, abaxial surface.*—RHS Fuchsia Purple 28/3.
- *Ray florets, color, fading to.*—RHS Rose Madder 23/3.
- *Disc florets, shape.*—Tubular, rounded at tip.
- *Disc florets, size, length.*—0.6 cm.
- *Disc florets, size, width.*—0.1 cm.
- *Number of disc florets per inflorescence.*—About 141.
- *Disc florets, color, immature.*—RHS Chinese Yellow 606.
- *Disc florets, color, mature.*—RHS Chinese Yellow 606/1 with an eye in the center of each disc which is RHS Imperial Purple 33/3.
- *Peduncle, aspect, strength.*—Stiff.
- *Peduncle, aspect, angle to stem.*—30°.
- *Peduncle, length, first peduncle.*—5.8 cm.
- *Peduncle, length, fourth peduncle.*—6.6 cm.
- *Peduncle, texture.*—Hirsute.
- *Peduncle, color.*—RHS Lavender Green ooo761.
- *Reproductive organs, androecium, floret location.*—Disc florets.
- *Anther color.*—RHS Maize Yellow 607/2.
- *Pollen, abundance.*—Abundant.
- *Pollen, color.*—RHS Straw Yellow 604.
- *Reproductive organs, gynoecium, floret location.*—Disc/ray florets.
- *Style color.*—RHS Straw Yellow 604/2.

Disease resistance: None Known.
Seed production: About 175 ovules/flower.
Winter hardiness: Hardy in zones 3–10 in uncovered field conditions without the need for added protection such as snow fences, mulch, etc.
Frost tolerance: Yes, extends blooming season to the first freeze in the north (In zones 3–4 the first frost usually takes place between September 1–15. In zones 3–4, the first freeze usually takes place between October 1–20).

What is claimed is:

1. A new and distinct cultivar of a Chrysanthemum plant named 92-296-25 substantially as herein shown and described, which:

(a) Exhibits extreme hybrid vigor (b) Develops, in its second and subsequent years after planting, when grown in the fall under natural day-length without the application of growth regulators, into a flowering herbaceous shrub having a plant height of from about 2.5 to about 3.0 feet and a spread from about 3.0 to about 7.0 feet, (c) Exhibits, in its second and subsequent years after planting and during the fall season (August–October), a massive floral display, (d) Displays flowers which are slightly toned gray, giving the flower petals a slightly altered coloration, (e) Exhibits superior winter hardiness, including frost tolerance, and (f) Exhibits self-pinching.

* * * * *